(12) United States Patent
Griffin et al.

(10) Patent No.: US 6,312,465 B1
(45) Date of Patent: Nov. 6, 2001

(54) HEART VALVE PROSTHESIS WITH A RESILIENTLY DEFORMABLE RETAINING MEMBER

(75) Inventors: Charles Durward Griffin, Leander; Louis A. Campbell; Tammi Elizabethy Klostermeyer, both of Austin, all of TX (US)

(73) Assignee: Sulzer Carbomedics Inc., Austin, TX (US)

( * ) Notice: Subject to any disclaimer, the term of this patent is extended or adjusted under 35 U.S.C. 154(b) by 0 days.

(21) Appl. No.: 09/360,093

(22) Filed: Jul. 23, 1999

(51) Int. Cl.[7] .................................................. A61F 2/24
(52) U.S. Cl. ........................................ 623/2.38; 623/2.18
(58) Field of Search ..................... 623/2.11, 2.2, 623/2.21, 2.22, 2.23, 2.24, 2.25, 2.3, 2.31, 2.33, 2.38, 2.41

(56) References Cited

U.S. PATENT DOCUMENTS

| | | | |
|---|---|---|---|
| 2,682,057 | * 6/1954 | Lord ...................................... | 623/2.38 |
| 4,506,394 | 3/1985 | Bedard ...................................... | 3/1.5 |
| 4,680,031 | 7/1987 | Alonso ...................................... | 623/2 |
| 5,332,402 | * 7/1994 | Teitelbaum .......................... | 623/2.38 |
| 5,370,685 | 12/1994 | Stevens ...................................... | 623/2 |
| 5,397,346 | * 3/1995 | Walker et al. ...................... | 623/2.38 |
| 5,411,552 | 5/1995 | Anderson et al. ........................ | 623/2 |
| 5,545,214 | 8/1996 | Stevens ...................................... | 623/2 |
| 5,607,465 | 3/1997 | Camilli ...................................... | 623/1 |
| 5,702,418 | 12/1997 | Ravenscroft .......................... | 606/198 |
| 5,716,370 | * 2/1998 | Williamson, IV et al. .......... | 606/153 |
| 5,725,552 | 3/1998 | Kotula et al. ......................... | 606/213 |
| 5,855,601 | 1/1999 | Bessler et al. ........................... | 623/2 |
| 6,045,576 | * 4/2000 | Starr et al. ............................. | 623/2.1 |
| 6,074,419 | * 6/2000 | Healy et al. ......................... | 623/2.12 |
| 6,092,529 | * 7/2000 | Cox ...................................... | 623/2.12 |

FOREIGN PATENT DOCUMENTS

0200926A2 * 3/1986 (EP) ..................................... 623/2.1

* cited by examiner

Primary Examiner—David H. Willse
Assistant Examiner—Suzette J. Jackson
(74) Attorney, Agent, or Firm—Blossom E. Loo; Timothy L. Scott

(57) ABSTRACT

A valve body assembly for being mounted adjacent an annulus within a heart. A first retainer is attached to the valve body assembly for engaging a first side of the annulus. A second retainer is attached to the valve body assembly and includes a resiliently-deformable retaining member for resiliently engaging a second side of the annulus. The resiliently deformable retaining member is collapsed to a size permitting it to be inserted into through the annulus and positioned adjacent the second side of the annulus. The retaining member is then allowed to expand such that it resiliently engages the second side of the annulus.

29 Claims, 4 Drawing Sheets

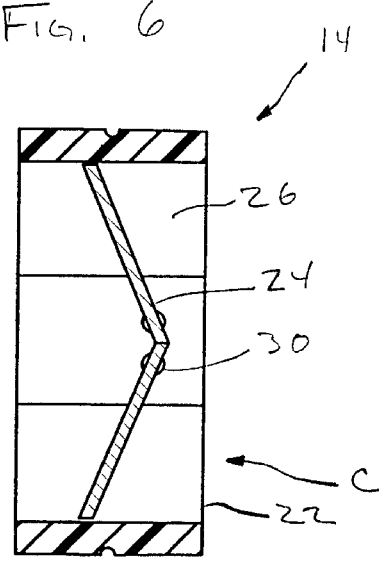
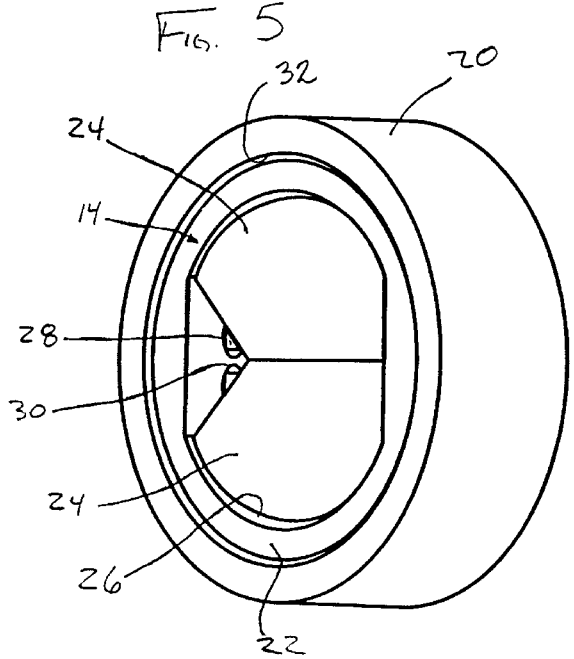
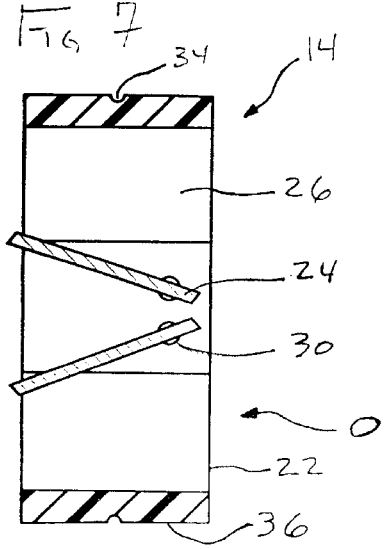
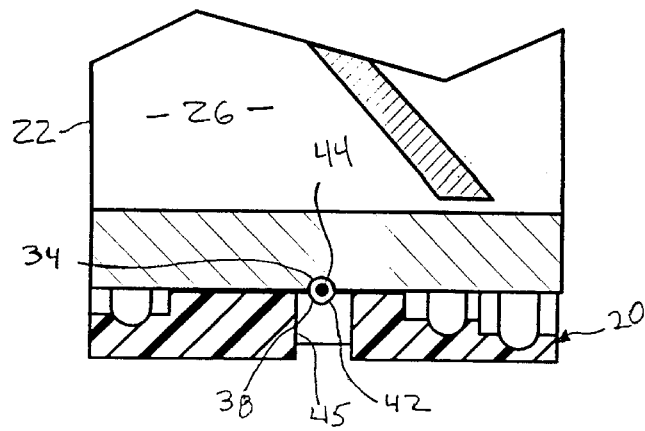

HEART VALVE PROSTHESIS WITH A RESILIENTLY DEFORMABLE RETAINING MEMBER

BACKGROUND

The disclosures herein relate generally to heart valves and more particularly to heart valves with a resiliently collapsible retainer.

Presently, the implantation of heart valves requires the surgeon to attach the heart valve to the annulus. One method of attachment is to use sutures. In most cases, the valve is attached using many interrupted sutures or one continuous suture. The use of sutures is time consuming as it requires the surgeon to tie numerous knots.

The technique of using sutures to secure the heart valve to the annulus occurs while the patient is on cardiac-by-pass. It is undesirable to keep a patient on cardiac-bypass for an extended period of time. By eliminating or reducing the need for sutures, the time to secure the valve to the annulus would be reduced. Thus, the time the patient is on cardiac-by-pass may also be reduced.

The space required for implanting prosthetic heart valve devices is limited. This is especially true in less invasive implantation procedures where a minimum incision size is a goal. For these types of implantation procedures, complex, space intensive attachment schemes are undesirable. This is also true in the cases of per- cutaneous insertion of a heart valve using a catheter based system.

U.S. Pat. No. 4,680,031 discloses a "tissue valve type" heart valve prosthesis which has a bio-compatible plastic sewing ring adapted to be surgically implanted into the mitral, aortic or tricuspid annulus of the human heart. The sewing ring has internal square threads and a bio-compatible fabric mesh or cloth that is embedded into the sewing ring so that the cloth can be fully wrapped around the sewing ring covering all of its plastic surfaces except for the internally protruding threads. A bio-compatible plastic stent support ring has externally disposed threads to lock with the threads of the sewing ring in approximately one turn, or less. The stent support ring also embeds a bio-compatible fabric mesh which can be wrapped around the stent support ring to cover all of its plastic surfaces, except for the protruding threads, and to form a cloth pocket wherein a solid stent is mounted.

U.S. Pat. Nos. 5,370,685 and 5,545,214 relate to a valve replacement system together with methods of preparation and use for endovascular replacement of a heart valve in a host. The valve replacement system includes up to five components: (1) a prosthetic valve device, (2) a valve introducer device, (3) an intraluminal procedure device, (4) a procedure device capsule, and (5) a tissue cutter. The system provides for endovascular removal of a malfunctioning valve and subsequent replacement with a permanent prosthetic heart valve.

U.S. Pat. No. 5,411,552 discloses a valve prosthesis for implantation in the body by use of a catheter. The valve includes a stent made from an expandable cylinder-shaped thread structure having several spaced apices. The elastically collapsible valve is mounted on the stent as the commissural points of the valve are secured to the projecting apices. The valve prosthesis can be compressed around the balloon of the balloon catheter and be inserted in a channel, for instance in the aorta. When the valve prosthesis is placed correctly, the balloon is inflated thereby expanding the stent and wedging it against the wall of aorta. The valve prosthesis and the balloon catheter make it possible to insert a cardiac valve prosthesis without a surgical operation that requires opening the thoracic cavity.

U.S. Pat. No. 5,607,465 discloses a valve for use in a blood vessel, internal to the blood vessel itself. The valve has a bent flexible wire mesh with elasticity and plasticity so as to be collapsible and implantable remotely at a desired site. The wire mesh is bent into three turns including two end turns and a central turn, in such a way as to confine a tubular space. The central turn is located at an angle relative to the end turns and mounts a monocusp sail-like valving element. A special catheter is used to collapse the flexible wire mesh to implant it remotely at the desired site and to restore the wire mesh to its original three-dimensional configuration.

U.S. Pat. No. 5,716,370 discloses a technique for replacing a heart valve using minimally invasive methods to reduce the time associated with replacing the valve. This technique includes a sutureless sewing cuff and a fastener delivery tool that holds the cuff against the patient's tissue while delivering two fasteners. The fasteners are delivered two at a time in opposite directions to attach the cuff to the tissue from the inside out. Drawstrings are operated from outside the patient's body and cinch the sewing cuff to the valve body. The cuff is releasably mounted on the tool. The tool stores a plurality of fasteners thereon. Two rows of staggered fasteners are formed whereby fasteners are located continuously throughout the entire circumference of the cuff.

U.S. Pat. No. 5,855,601 discloses an artificial heart valve including a relatively rigid stent member having a first cylindrical shape and a flexible valve disposed in the stent member. The stent member is self-expandable to a second cylindrical shape and collapsible to its first cylindrical shape. The valve comprises a circular portion comprising a plurality of leaflets extending from the periphery of the circular portion towards the center thereof. The leaflets are configured to allow for flow of blood through the valve in one direction only. The diameter of the circular portion is substantially the same as the inside diameter of the stent member when the stent member is in its second cylindrical shape. The valve member is attached to the stent member.

Although attempts have been made to reduce the time and space required for implantation, these attempts have provided only limited success. Accordingly, there is a need for an improved heart valve prosthesis that overcomes the shortcomings of present heart valves.

SUMMARY

One embodiment, accordingly, provides a heart valve that can be secured to the annulus using fewer sutures, and preferably using no sutures. To this end, a heart valve prosthesis includes a valve body assembly for being mounted adjacent an annulus within a heart. A first retainer is attached to the valve body assembly for engaging a first side of the annulus. A second retainer is attached to the valve body assembly and includes a resiliently deformable retaining member for resiliently engaging a second side of the annulus.

A key advantage of heart valves according to the embodiments presented herein is that the time required to implant the heart valve can be reduced significantly.

BRIEF DESCRIPTION OF THE DRAWING FIGURES

FIG. 5 is a perspective view illustrating an embodiment of a valve assembly mounted in a stiffening member.

FIG. 6 is a cross-sectional view illustrating an embodiment of a valve assembly with leaflets in the closed position.

FIG. 7 is a cross-sectional view illustrating an embodiment of a valve assembly with leaflets in the open position.

FIG. 8 is an expanded cross-sectional view illustrating an embodiment of a valve body mounted in a stiffening member.

DETAILED DESCRIPTION

Figure 1A:
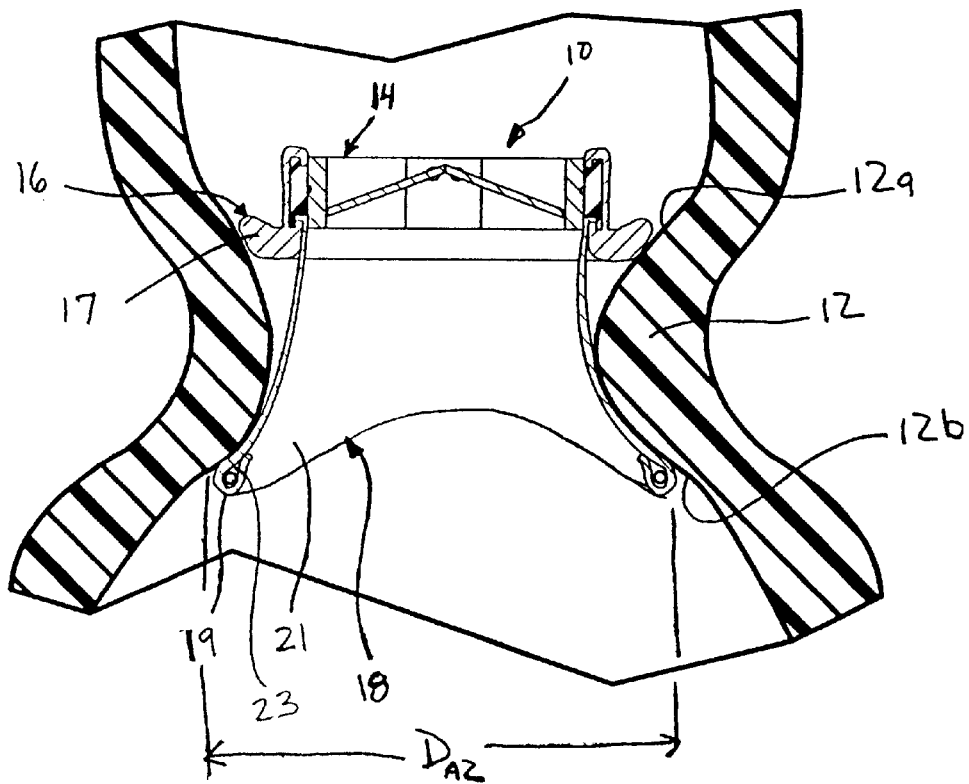
FIG. 1A is a cross sectional view illustrating an embodiment of a heart valve assembly installed in a supra-annular position.
Figure 1B:
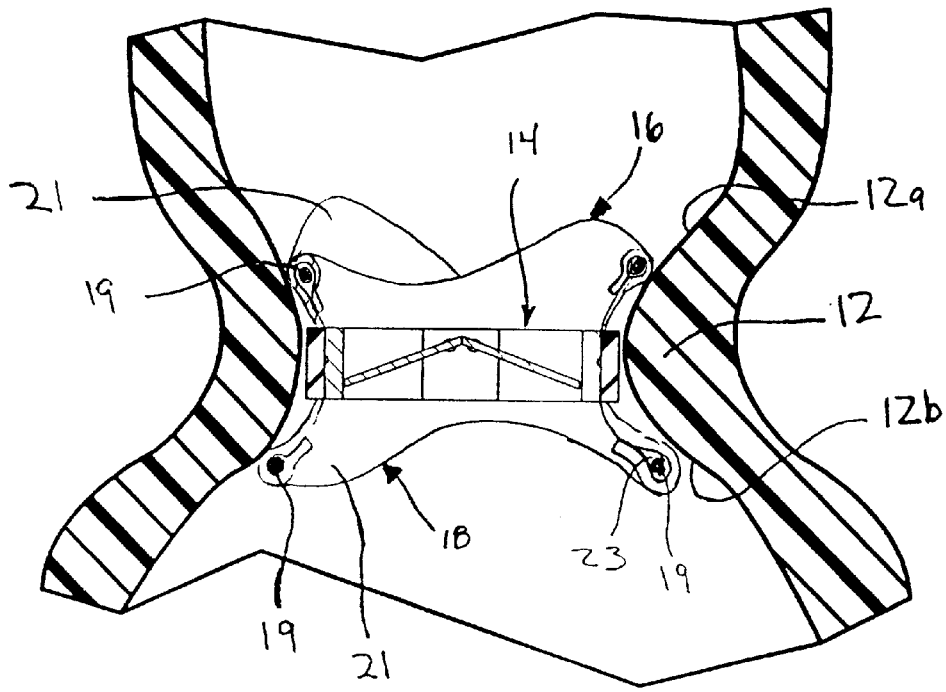
FIG. 1B is a cross sectional view illustrating an embodiment of a heart valve assembly installed in an inter-annular position.

FIG. 1A illustrates an embodiment of a heart valve 10 implanted within an annulus 12 of a heart in a supra-annular position. FIG. 1B illustrates an embodiment of a heart valve 10 implanted within the annulus 12 in an inter-annular orientation.

As illustrated in FIGS. 1A and 1B the heart valve 10 according to the present embodiments includes a valve assembly 14, a first retainer 16 and a second retainer 18 attached thereto. In FIG. 1A, the first retainer 16 includes a polymer plug 17 that forms a hemostatic seal with a first side 12a of the annulus 12 during diastolic pressure. The second retainer 18 includes a retaining member 19 and skirt 21 for forming a hemostatic with a second side 12b of the annulus 12 during systolic flow. In FIG. 1B, the first retainer 16 is constructed similar to the second retainer 18, including the retaining member 19 and skirt 21.

Figure 2:
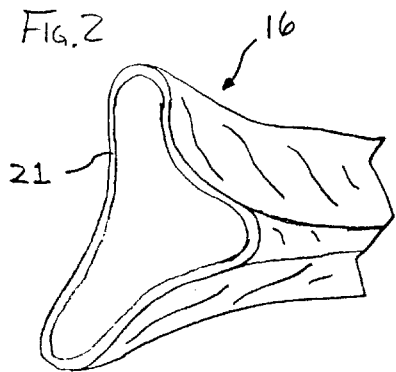
FIG. 2 is a perspective view illustrating an embodiment of a retainer formed to define a tri-lobe shape.
Figure 3:
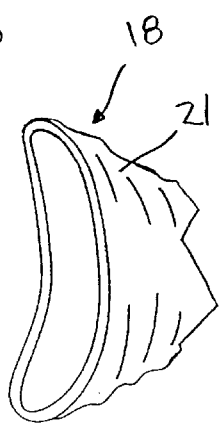
FIG. 3 is a perspective view illustrating an embodiment of a retainer formed to define a bi-lobe shape.

In a preferred embodiment, the first retainer 16 of FIG. 1B is formed to provide a tri-lobe shape illustrated in FIG. 2, and the second retainer 18 of FIG. 1B is formed to provide a bi-lobe shape illustrated in FIG. 3. The tri-lobe shape aids in minimizing the potential for interference with the anatomy of the heart on the first side 12a of the annulus 12 (i.e. sinus valsalva). The bi-lobe shape aids in minimizing the potential for interference with the anatomy on the second side 12b of the annulus 12 (i.e. ventricle).

Figure 4A:
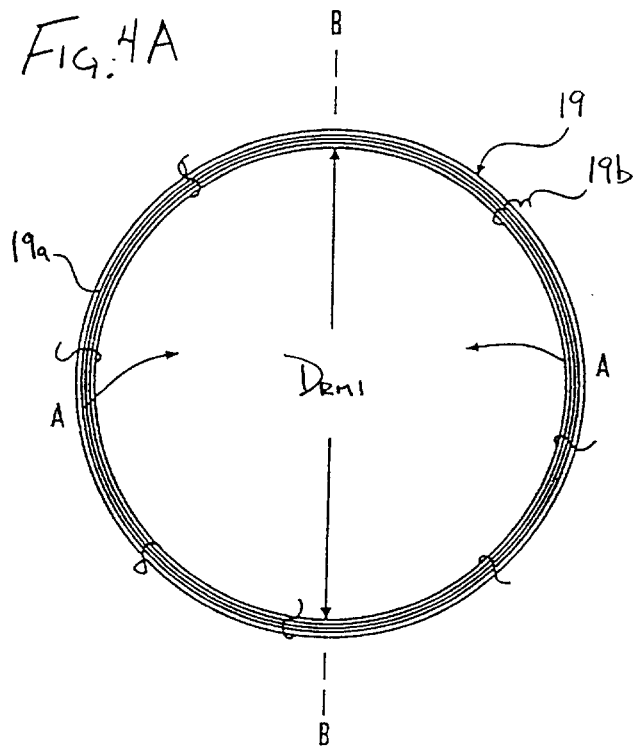
FIG. 4A is a top view illustrating an embodiment of a retaining member in an undeformed configuration.
Figure 4B:
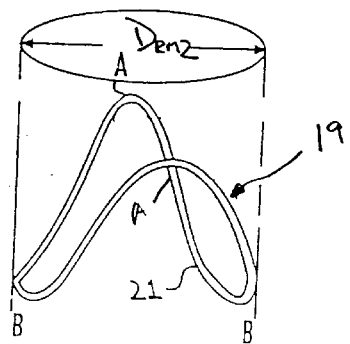
FIG. 4B is a perspective view illustrating an embodiment of a deformed retaining member.

As illustrated in FIGS. 4A and 4B, one embodiment of the retaining member 19 is formed of a plurality of strands 19a wrapped to form a coil. The retaining member 19 may be formed by wrapping a single length of wire around a mandrel and bundling it with one or more ties 19b. The ties 19b may be formed of surgical suture material or other suitable material. The retaining member 19 may be formed by a variety of other materials such as helically intertwined multiple strand wires or polymeric filament material. A broad range of bio-compatible materials capable of forming a highly resilient retaining member may be used.

The number of strands 19a can be varied according to the type of material used and the particular application involved. However, in one embodiment, the number of strands 19a utilized is approximately 8 to 10. The number of strands 19a may be as few as 2 or as many as 100 or more.

While a variety of different wire diameters may be used, the individual strands 19a may have a diameter of from about 0.05 mm to a bout 0.10 mm. In one preferred embodiment, the strands 19a are formed of a wire having a diameter of about 0.10 mm. The strands 19a may be made of any highly resilient metal or polymeric material, including a nickel-titanium alloy such as the product sold under the name Nitinol. Generally, the resilient, superelastic or martensitic form of Nitinol is utilized.

As best illustrated in FIGS. 4A and 4B, the retaining member 19 has an undeformned diameter $D_{RM1}$ larger than a diameter $D_{A2}$, FIG. 1B, of the second side 12b of the annulus 12. The difference in the undeformed diameter $D_{RM1}$ and the diameter $D_{A2}$ of the second side 12b of the annulus 12 results in the retaining member 19 continually applying a force on the interior surface of the annulus 12. The various diameters of the retaining member 19 are subject to considerable variation depending on the particular body passage and host involved.

To facilitate implanting the heart valve 10, the retaining member 19 is configured to be deformable to a diameter $D_{RM2}$ that is equal to or smaller than the diameter $D_{A2}$ of the annulus 12, FIG. 1. Two opposed points "A", FIGS. 4A and 4B, on the retaining member 19 may be deflected towards each other, causing the retaining member 19 to fold along its diametric axis B. In this configuration, the retaining member 19 may be inserted through the annulus 12.

As best illustrated in FIG. 1, the retaining member 19 resides in a pocket 23 formed in the skirt 21. The skirt 21 may be formed of any one of a variety of bio-compatible materials. For example, the skirt may be formed of a flexible woven or knitted textiles made of materials sold under the names Dacron, Teflon or other bio-compatible materials. Various techniques such as a stitching process using thread may be used to form the pocket 23.

In FIG. 5, the valve assembly 14 is mounted within a stiffening member 20. The valve assembly 14 includes a valve body 22 and two leaflets 24 pivotally mounted in a central passage 26 of the valve body 22. The leaflets 24 include protruding members 28 captured within apertures 30 formed in an interior surface of the central passage 26. The leaflets 24 may pivot between a closed position C, FIG. 6, during diastolic pressure, and an open position O, FIG. 7, during systolic flow.

Referring to FIG. 5, the stiffening member 20 includes a bore 32 in which the valve assembly 22 is received. The valve body 22 includes a groove 34 formed in an outer surface 36, FIG. 7, of the valve body 22. The stiffening member 20 includes a mating groove 38, FIG. 9, formed in an inner surface 40 of bore 32.

As best illustrated in FIG. 8, the groove 34 and mating groove 38 form a channel 42 for receiving a retaining member 44 such as a wire. The retaining member 44 is inserted into the channel 42 through a window 45 formed through the stiffening member. see also FIG. 9. The retaining member 44, FIG. 8 limits axial displacement of the valve body 22 relative to the stiffening member 20. The groove 34 and the mating groove 38 may be configured such that the channel 42 extends around the entire circumference of the valve body 22 or around a portion of its circumference.

Figure 9:
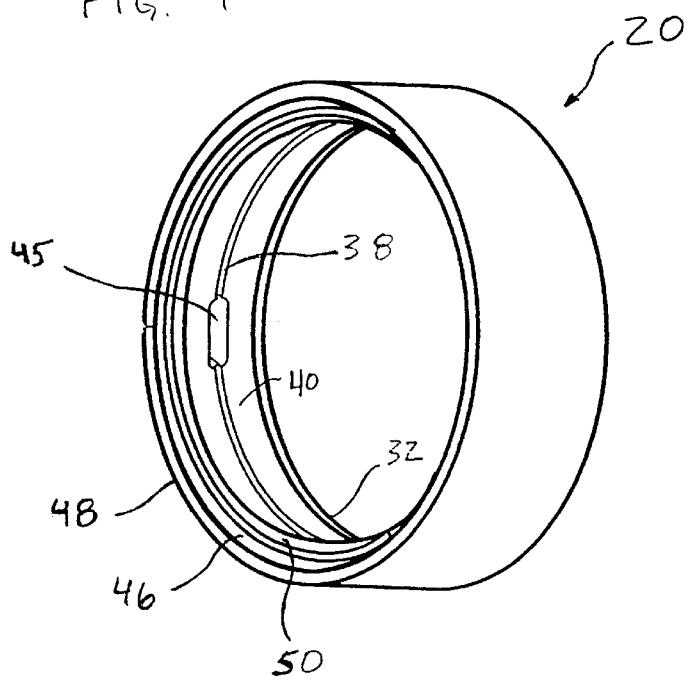
FIG. 9 is a perspective view illustrating an embodiment of a stiffening member.
Figure 10:
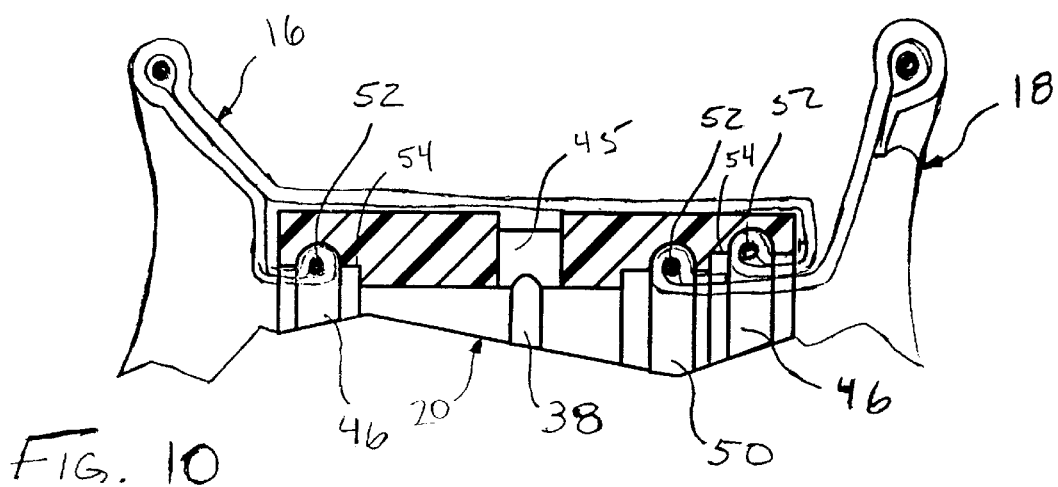
FIG. 10 is a cross-sectional illustrating an embodiment of a stiffening, member, a first retainer and a second retainer.

Referring now to FIGS. 9 and 10, the stiffening member 20 includes a groove 46 adjacent each edge 48 of the stiffening member 20 and a groove 50 at a position set back from the edge 48. The grooves 46, 50 are configured for receiving a retainer 52 such as a snap ring for attaching the skirts of the first and second retainers 16, 18 to the stiffening member 20.

A recess 54, FIG. 10, is provided adjacent the grooves 46, 50 in the stiffening member 20. The recess 54 allows for the valve body 24 to be inserted into the bore 34 of the stiffening member 20 without interference with the skirts of the retainers.

In operation, the retention member of the second retainer is resiliently deformed to a diameter smaller than the diameter of the annulus. The second retainer is inserted through the annulus to a position wherein the first retainer engages the first side of the annulus. The retention member of the second retainer is released, allowing it to expand to a recovered diameter larger than the diameter of the annulus at the second side yet smaller than the undeformed diameter of the retention member. The first and second retainers form hemostatic seals with the first and second sides of the annulus, respectively, during diastolic pressure and systolic flow. The retaining member has an undeformed diameter larger than the diameter of the second side of the annulus. The difference in these diameters results in the retaining member applying a constant force on the engaged surface of the annulus.

As a result, one embodiment provides a heart valve prosthesis including a valve body assembly for being mounted adjacent an annulus within a heart. A first retainer is attached to the valve body assembly for engaging a first side of the annulus. A second retainer is attached to the valve body assembly and includes a resiliently-deformable retaining member for resiliently engaging a second side of the annulus.

Another embodiment provides a heart valve prosthesis including a valve body assembly for being mounting adjacent an annulus within a heart. A first retaining means is attached to the valve body assembly for engaging a first side of the annulus. A resiliently-deformable second retaining means is attached to the valve body assembly for resiliently engaging a second side of the annulus.

A further embodiment provides a method of making a heart valve prosthesis including forming a valve body assembly having a stiffening member and a valve body mounted within the stiffening member. A first retainer is attached to the valve body assembly for engaging a first side of the annulus. A resiliently-deformable retaining member is attached to the valve body for engaging a second side of the annulus.

Several advantages are achieved by a heart valve according to the embodiments presented herein. The number of sutures required to secure the sewing cuff is greatly reduced. As a result, the implantation time is significantly reduced. This reduction in implantation time beneficially reduces the time that the patient is on cardiac-by-pass.

Although illustrative embodiments have been shown and described, a wide range of modification, change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A heart valve prosthesis, comprising:
   a valve body assembly for being mounted adjacent an annulus within a heart;
   a first retainer attached to the valve body assembly for engaging a first side of the annulus; and
   a second retainer attached to the valve body assembly, the second retainer including a resiliently-deformable retaining member for resiliently engaging a second side of the annulus.

2. A heart valve prosthesis, comprising:
   a valve body assembly for being mounted adjacent an annulus within a heart;
   a first retaining means attached to the valve body assembly for engaging a first side of the annulus; and
   a resiliently-deformable second retaining means attached to the valve body assembly for resiliently engaging a second side of the annulus.

3. A method of making a heart valve prosthesis, comprising the steps of:
   forming a valve body assembly including a stiffening member and a valve body mounted within the stiffening member;
   attaching a first retainer to the valve body assembly for engaging a first side of the annulus; and
   attaching a second retainer having a resiliently-deformable retaining member to the valve body for engaging a second side of the annulus.

4. The method of claim 3 wherein the step of attaching the second retainer to the valve body assembly includes the step of attaching a first end of a skirt to the valve body assembly and attached a second end of the skirt to the retaining member.

5. The method of claim 3 further comprising the step of forming the retaining, member.

6. The method of claim 5 wherein the step of forming the retaining member includes the step of forming the retaining member to define a bi-lobe shape.

7. The method of claim 5 wherein the step of forming the retaining member includes the step of forming a bundled coil of wire windings.

8. A heart valve prosthesis, comprising:
   a valve body assembly for mounting adjacent an annulus within a heart;
   a first retainer attached to the valve body assembly for engaging a first side of the annulus;
   a second retainer attached to the valve body assembly, the second retainer including a resiliently-deformable retaining member for resiliently engaging a second side of the annulus; and
   the valve body assembly includes a stiffening member and a valve body mounted within the stiffening member.

9. The heart valve prosthesis of claim 8, wherein the retaining member has an annular shape.

10. The heart valve prosthesis of claim 8, wherein the second retainer includes a first end having a skirt attached to the valve body assembly and a second end attached to the retaining member.

11. The heart valve prosthesis of claim 10, wherein the skirt is formed of a fabric material.

12. The heart valve prosthesis of claim 8, wherein the second retainer is formed to define a bi-lobe shape.

13. The heart valve of claim 8, wherein the first retainer is formed to define a tri-lobe shape.

14. The heart valve of claim 13, wherein the first retainer is a polymeric plug.

15. The heart valve prosthesis of claim 8, wherein the second side of the annulus is adjacent a ventricle chamber.

16. The heart valve prosthesis of claim 12, wherein the first retainer is a fabric cuff.

17. The heart valve prosthesis of claim 8, wherein the retaining member is a bundled coil of wire windings.

18. The heart valve prosthesis of claim 8, wherein the first retainer is attached to the valve body assembly in a manner enabling the valve body to be mounted in an intra-annular position.

19. The heart valve prosthesis of claim 8, wherein the first retainer is attached to the valve body assembly in a manner enabling the valve body to be mounted in an supra-annular position.

20. The heart valve prosthesis of claim 8, wherein the annulus has a respective diameter and wherein the retaining member has a deformed diameter less than the respective diameter of the annulus.

21. A heart valve prosthesis, comprising:

a valve body assembly for being mounted adjacent an annulus within a heart;

a first retainer attached to the valve body assembly for engaging a first side of the annulus; and a second retainer attached to the valve body assembly, the second retainer including a resiliently-deformable retaining member for resiliently engaging a second side of the annulus, wherein the second retainer including a first end having a skirt formed from a fabric material, attached to the valve body assembly and a second end attached to the retaining member.

22. A heart valve prosthesis, comprising:

a valve body assembly for being mounted adjacent an annulus within a heart;

a first retainer attached to the valve body assembly for engaging a first side of the annulus; and a second retainer attached to the valve body assembly, the second retainer including a resiliently-deformable retaining member for resiliently engaging a second side of the annulus and is formed to define a bi-lobe shape.

23. A heart valve prosthesis, comprising:

a valve body assembly for being mounted adjacent an annulus within a heart;

a first retainer attached to the valve body assembly for engaging a first side of the annulus and is formed to define a tri-lobe shape, and a second retainer attached to the valve body assembly, the second retainer including a resiliently-deformable retaining member for resiliently engaging a second side of the annulus.

24. A heart valve prosthesis, comprising:

a valve body assembly for being mounted adjacent an annulus within a heart;

a first retainer attached to the valve body assembly for engaging a first side of the annulus, formed to define a tri-lobe shape and is a polymeric plug; and a second retainer attached to the valve body assembly, the second retainer including a resiliently-deformable retaining member for resiliently engaging a second side of the annulus.

25. A heart valve prosthesis, comprising:

a valve body assembly for being mounted adjacent an annulus within a heart;

a first retainer attached to the valve body assembly for engaging a first side of the annulus and is a fabric cuff; and a second retainer attached to the valve body assembly, the second retainer including a resiliently-deformable retaining member for resiliently engaging a second side of the annulus and is formed to define a bi-lobe shape.

26. A heart valve prosthesis, comprising:

a valve body assembly for being mounted adjacent an annulus within a heart;

a first retainer attached to the valve body assembly for engaging a first side of the annulus; and a second retainer attached to the valve body assembly, the second retainer including a resiliently-deformable retaining member made of a bundled coil of wire windings for resiliently engaging a second side of the annulus.

27. A heart valve prosthesis, comprising:

a valve body assembly for being mounted adjacent an annulus within a heart;

a first retainer attached to the valve body assembly for engaging a first side of the annulus and in a manner enabling the valve body to be mounted in an supra-annular position; and a second retainer attached to the valve body assembly, the second retainer including a resiliently-deformable retaining member for resiliently engaging a second side of the annulus.

28. A heart valve prosthesis, comprising:

a valve body assembly for being mounted adjacent an annulus within a heart;

a first retainer attached to the valve body assembly for engaging a first side of the annulus; and a second retainer attached to the valve body assembly, the second retainer including a resiliently-deformable retaining member for resiliently engaging a second side of the annulus, the first and second retainers each capable of forming a hemostatic seal with the annulus.

29. A heart valve prosthesis, comprising:

a valve body assembly for being mounted adjacent an annulus within a heart;

a first retainer attached to the valve body assembly for engaging a first side of the annulus; and a second retainer attached to the valve body assembly, the second retainer including a resiliently-deformable retaining member for resiliently engaging a second side of the annulus having a diameter $D_{A2}$, the resiliently-deformable retaining member having an undeformed diameter $D_{RM1}$ larger than $D_{A2}$ and a deformable diameter $D_{RM2}$ equal to or smaller than $D_{A2}$.

* * * * *